US006743962B2

United States Patent
O'Rear et al.

(10) Patent No.: US 6,743,962 B2
(45) Date of Patent: *Jun. 1, 2004

(54) PREPARATION OF HIGH OCTANE ALKYLATE FROM FISCHER-TROPSCH OLEFINS

(75) Inventors: Dennis J. O'Rear, Petaluma, CA (US); Steven S. Mathur, Danville, CA (US); Thomas Van Harris, Benicia, CA (US); Curtis L. Munson, Oakland, CA (US); Cong-Yan Chan, Kensington, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/059,388

(22) Filed: Jan. 31, 2002

(65) Prior Publication Data

US 2003/0166982 A1 Sep. 4, 2003

(51) Int. Cl.[7] .................................................. C07C 2/56
(52) U.S. Cl. ........................ 585/717; 585/709; 585/323; 208/950
(58) Field of Search ............................... 585/709, 717, 585/323; 208/950

(56) References Cited

U.S. PATENT DOCUMENTS

| | | | |
|---|---|---|---|
| 2,452,121 A | * | 10/1948 | Grahame .................... 518/719 |
| 2,564,072 A | * | 8/1951 | Lien et al. .................. 208/141 |
| 2,581,102 A | * | 1/1952 | Hodges ....................... 208/263 |
| 2,918,486 A | * | 12/1959 | Binning et al. ............. 208/263 |
| 3,723,564 A | | 3/1973 | Tidwell et al. |
| 3,972,958 A | * | 8/1976 | Garwood et al. ........... 208/414 |
| 4,041,096 A | | 8/1977 | Kuo |
| 4,041,097 A | * | 8/1977 | Ireland et al. ................ 208/79 |
| 4,044,063 A | * | 8/1977 | Ireland et al. ................ 208/79 |
| 4,046,830 A | | 9/1977 | Kuo |
| 4,049,741 A | | 9/1977 | Kuo et al. |
| 4,111,792 A | | 9/1978 | Caesar et al. |
| 4,132,745 A | | 1/1979 | Amigues et al. |
| 4,234,412 A | * | 11/1980 | Boersma et al. ............ 502/258 |
| 4,260,841 A | | 4/1981 | Holland et al. |
| 4,279,830 A | | 7/1981 | Haag et al. |
| 4,367,356 A | | 1/1983 | Ward |
| 4,398,050 A | | 8/1983 | Hofstadt et al. |
| 4,447,664 A | * | 5/1984 | Murchison et al. ......... 585/323 |
| 4,547,601 A | | 10/1985 | Holland et al. |
| 5,654,251 A | | 8/1997 | Abbott et al. |
| 5,792,896 A | | 8/1998 | Randolph et al. |
| 6,194,625 B1 | | 2/2001 | Graves et al. |
| 6,333,442 B1 | | 12/2001 | Cosyns et al. |

FOREIGN PATENT DOCUMENTS

NL 1021320 8/2003

OTHER PUBLICATIONS

Perry, *Chemical Engineers' Handbook*, 4th Edition, section 13, pp. 46–55.
Munson et al, "Factors Influencing Solvent Selection for Extraction of Ethanol from Aqueous Streams"; *I&EC Process Design and Development*, 1984, vol. 23, pp. 109–115.
Netherlands Search Report mailed Sep. 23, 2003.
Search Report issued in British Application No. GB 0300087.4, Jul. 17, 2003.

* cited by examiner

Primary Examiner—Walter D. Griffin
(74) Attorney, Agent, or Firm—Burns, Doane, Swecker & Mathis, L.L.P.

(57) ABSTRACT

A Fischer-Tropsch $C_3$–$C_4$ olefin stream is treated to lower the oxygenate content to below 4000 ppm. Another Fischer-Tropsch fraction is hydrotreated and hydrocracked to provide an isobutane-containing stream. The treated $C_3$–$C_4$ olefin stream is reacted with the isobutane stream in an alkylation reactor to provide a highly branched, high octane isoparaffinic alkylate. The alkylate is useful as a blending component in motor gasoline.

15 Claims, 1 Drawing Sheet

Preparation of High Octane Alkylate From
Fischer Tropsch-Derived Products

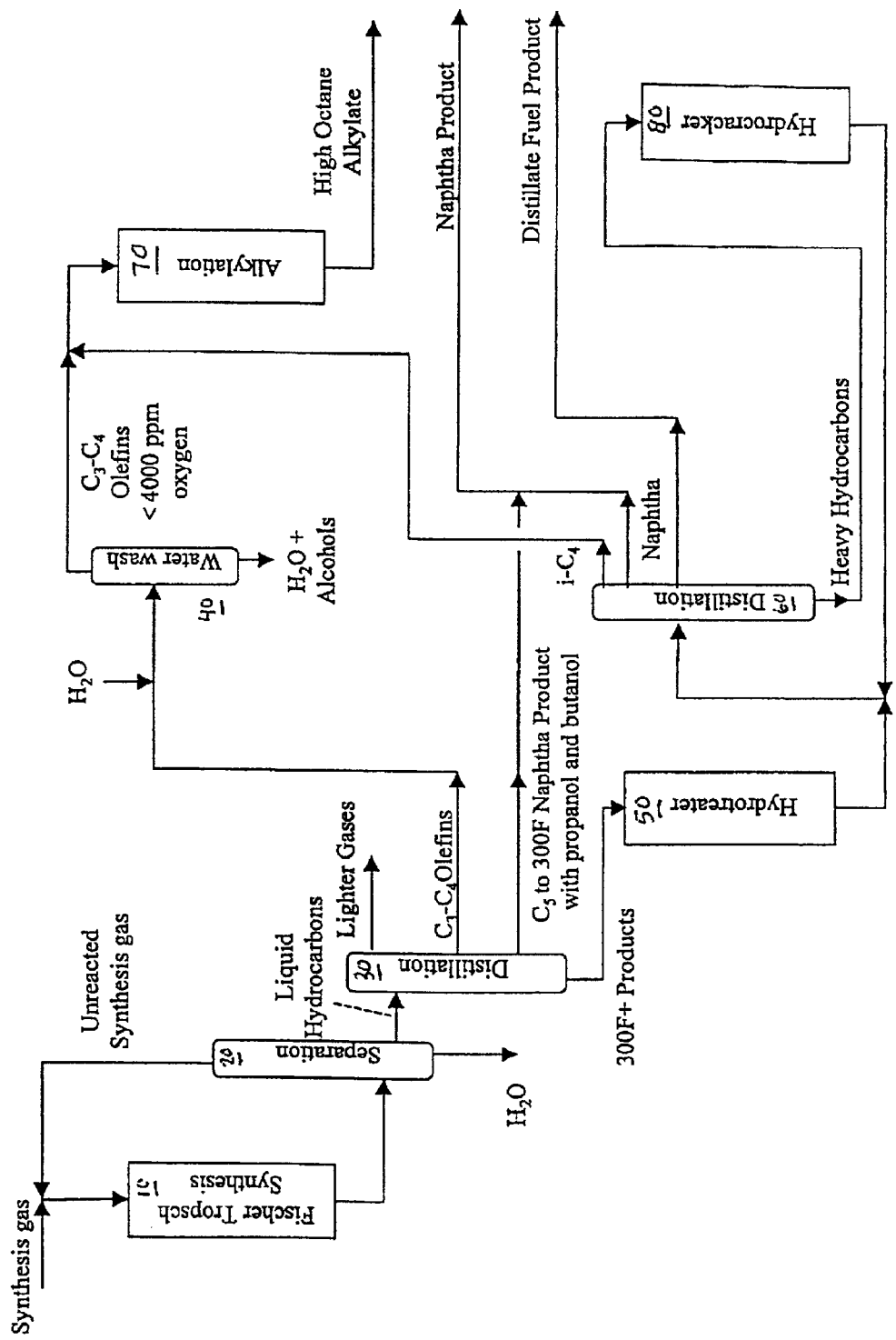

PREPARATION OF HIGH OCTANE ALKYLATE FROM FISCHER-TROPSCH OLEFINS

CROSS REFERENCE TO RELATED APPLICATIONS

The present application is related to application Ser. No. 10/059,252, filed concurrently herewith, entitled MANUFACTURE OF HIGH OCTANE ALKYLATE. The disclosure of said related application is incorporated herein in its entirety.

BACKGROUND OF THE INVENTION

1. Field of the Invention

The present invention relates generally to a process for converting Fischer-Tropsch light olefin-containing fractions into alkylates. More particularly, this invention relates to a process for obtaining high octane alkylates by reacting Fischer-Tropsch light olefins containing low levels of oxygenates with isoparaffins.

2. Description of Related Art

Because of their high octane numbers and low vapor pressures, alkylates have been used for many years as blending components in motor gasolines. The alkylation process involves the reaction of light olefins such as propylene and butylene with isoparaffins such as isobutane and isopentane in the presence of an acid catalyst such as $H_2SO_4$ and HF to form highly branched, isoparaffinic products known as alkylates. Typical sources for light olefins include catalytic crackers, cokers and vis-breakers.

The Fischer-Tropsch process also produces light olefins. The process involves reacting synthesis gas composed mainly of CO and $H_2$ in the presence of a suitable catalyst to form a variety of predominantly linear hydrocarbonaceous solid, liquid and gaseous products. Some of these products can be refined using known procedures such as hydrotreating, hydrocracking and hydroisomerization to yield moderately branched, isoparaffin-rich middle distillate fuels such as diesel and jet fuels. A gaseous phase produced in a Fischer-Tropsch synthesis, upon condensation and subsequent distillation, produces a light olefin product composed primarily of $C_3$–$C_4$ olefins. However, this product is considered to be poorly suited for use as a feedstock for conversion to alkylates for a number of reasons.

Products of Fischer-Tropsch syntheses normally contain relatively high levels of oxygenates, frequently in amounts above 4000 ppm oxygenate. Oxygenates can react to form water which dilutes the acid catalysts conventionally used in alkylation. Accordingly, light olefin feedstocks for alkylation should contain no more than 4000 ppm oxygenate, preferably much less. Also, light olefin streams from Fischer-Tropsch processes contain relatively low levels of isobutane. As such, they do not constitute a good source for isobutane. In the alkylation process, isobutane feedstocks should contain at least 30% by weight, preferably up to 75% by weight isobutane. Also, Fischer-Tropsch light olefin streams are composed predominantly of 1-butene. Feeds containing 1-butene normally yield alkylates with lower octane numbers than 2-butene. Desirably, the ratio of 2-butene to total butenes in the feed for alkylation should be at least 0.1 and most preferably at least 0.5.

Hydroisomerization processes have been used to produce moderately branched iosparaffins in the distillate fuel boiling range. However, they cannot be used to produce high-octane, highly branched isoparaffins in the gasoline boiling range. If hydroisomerization processes are run in a severe mode in an attempt to create highly branched products instead of moderately branched products, the feedstock cracks to form excessive amounts of undesirable light gases. Accordingly, the only practical method to manufacture high octane, highly branched, gasoline boiling range isoparaffins is by alkylation.

Consideration has been given to converting Fischer-Tropsch $C_3$–$C_4$ olefin streams into a feedstock suitable for alkylation by total hydrogenation or by using known treatments to lower the oxygenate content to an acceptable level. However, these approaches would necessitate a separate step to isomerize butane while hydrogenation would saturate the olefins in the $C_4$ stream. Also, the oxygenates removed from the $C_3$–$C_4$ stream would not be converted into alkylates. What is needed is an economical process for converting a $C_3$–$C_4$ light olefin fraction from a Fischer-Tropsch process into a highly branched isoparaffin mixture suitable as a blending component to prepare high octane gasolines.

Alkylation using light olefins obtained via a Fischer-Tropsch synthesis are described in U.S. Pat. Nos. 4,279,830; 4,046,830; and 4,049,741. These patents do not disclose using a $C_3$–$C_4$ olefin-containing feed which has been processed to reduce oxygenate levels to below 4000 ppm oxygenate.

It is an object of the invention to provide a process for economically preparing high octane alkylates from a Fischer-Tropsch $C_3$–$C_4$ light olefin stream having reduced oxygenate levels.

It is another object of the invention to utilize a Fischer-Tropsch $C_3$–$C_4$ olefin fraction with reduced oxygenate levels and an isobutane stream obtained by hydrocracking a Fischer-Tropsch 300° F.+ product to produce a high octane alkylate.

These and other objects of the present invention will become apparent to the skilled artisan upon a review of the following description, the claims appended hereto and the Figures of the drawings.

SUMMARY OF THE INVENTION

The objectives of the invention are attained by a process which includes the following steps:

(a) recovering a light $C_3$–$C_4$ olefin product stream from a Fischer-Tropsch reactor;

(b) processing the $C_3$–$C_4$ olefin stream to reduce the level of oxygenates to less than 4000 ppm oxygen;

(c) hydrocracking a $C_5$+ product from a Fischer-Tropsch synthesis to generate an isobutane-containing stream;

(d) blending the product stream from step (b) with the product stream from step (c);

(e) reacting the blend of step (d) in the presence of an alkylation catalyst; and (f) recovering a highly branched, isoparaffinic alkylate having a research octane number greater than 80.

Key features of the invention include processing a Fischer-Tropsch $C_3$–$C_4$ olefin stream to be used in an alkylation reaction so that it contains no more than about 4000 ppm oxygenate and preferably less than 1000 ppm, and processing a $C_5$+ Fischer-Tropsch product to produce a feed for alkylation containing at least 30% by weight isobutane. Thus, both feeds to the alkylation reactor are obtained from a Fischer-Tropsch reaction. Preferred techniques for reducing oxygenate levels include extractive or azeotropic distillation, decarboxylation, adsorption and water extraction or water washing. Alcohols recovered from the Fischer- Tropsch process can be dehydrated to provide additional $C_3$–$C_4$ olefins. Also, 1-butenes present in the olefin stream can be isomerized to 2-butenes to improve the octane number.

BRIEF DESCRIPTION OF THE FIGURE OF THE DRAWING

The FIGURE is a schematic flow diagram of one embodiment of the invention.

DETAILED DESCRIPTION OF PREFERRED EMBODIMENTS OF THE INVENTION

The present invention uses products from a Fischer-Tropsch synthesis to obtain alkylates having a research octane number of at least 80, preferably at least 85 and most preferably at least 90. As indicated earlier, the Fischer-Tropsch synthesis generally involves reacting a syngas composed primarily of CO and $H_2$ in the presence of a catalyst under suitable temperatures and pressures to yield a variety of gaseous, liquid and solid products composed primarily of hydrocarbonaceous materials. Any source of hydrocarbon can be used to generate the syngas: natural gas, coal and petroleum products. The reaction can be conducted in a variety of reactors including fixed bed reactors, slurry reactors, fluidized bed reactors or a combination of different types of reactors. Typical reaction conditions include temperatures ranging from about 300°–700° F., pressures ranging from about 10–600 psia and catalyst space velocities ranging from about 100–10000 cc/g/hr. Mole ratios of hydrogen to carbon monoxide may range from about 0.5–4. Suitable catalysts include one or more Group VIII catalytic metals such as Fe, Ni, Co, Ru, and Re. An example of a typical Fischer-Tropsch catalyst comprises Co and one or more of Re, Ru, Fe, Ni, Th, Zr, Hf, U, Mg and La on a suitable inorganic support.

The effluent stream from the Fischer-Tropsch reactor is processed to recover a light olefin stream. A wide variety of products is generated in a Fischer-Tropsch synthesis. These include a gaseous phase and a liquid waxy phase. The gaseous phase is cooled in a separation zone to condense the hydrocarbons. Unreacted syngas is recycled back to the Fischer-Tropsch reactor. Water present in the condensate is removed by using known techniques, such as by density differences. The condensate alone or admixed with the waxy phase is forwarded to a distillation zone.

As indicated, the Fischer-Tropsch process generates a wide range of generally linear hydrocarbonaceous products. The atmospheric boiling point of some of these products is shown below.

| Compound | Boiling point at atmospheric pressure, ° C./° F. |
|---|---|
| Carbon monoxide | −191/−312 |
| Carbon dioxide | −78/−61 (solid) |
| Propylene | −48/−54 |
| Propane | −42/−44 |
| 1-butene | −6/21 |
| n-Butane | −0.5/31 |
| n-Pentane | 36/97 |
| Oxygenates: | |
| Methanol | 39/102 |
| Ethanol | 78/172 |
| 1-propanol | 97/207 |

-continued

| Compound | Boiling point at atmospheric pressure, ° C./° F. |
|---|---|
| 1-butanol | 117/243 |
| Acetic Acid | 118/244 |
| Propanoic Acid | 144/291 |
| Butanoic acid | 164/327 |

It is evident that a $C_3$ and/or $C_4$ fraction can be obtained from this effluent by distillation. The cut point of the distillation should be high enough to include butenes, but low enough to exclude traces of methanol. This means that the end point of the $C_3$–$C_4$ fraction should be between −6 and 39° C., preferably between 0 and 30° C., most preferably between 10 and 20° C. Simple distillation normally is not effective in generating a $C_3$–$C_4$ fraction having an oxygenate content below 4000 ppm as azeotropes may be formed. If the oxygenate content is in excess of 4000 ppm after simple distillation, other techniques may be used to lower the oxygenate content including azeotropic distillation, extractive distillation, water washing or combinations thereof. It should be understood that oxygen is present as oxygenates and that oxygenate contents are on a water-free and air-free basis. The term "oxygenates" as used herein refers to any carbon and oxygen-containing hydrocarbon compound. Examples of oxygenates include alcohols, acids, aldehydes, esters, ketones and the like.

The boiling range of a C3–C4 fraction may be suitably determined using an ASTM D2887 procedure, taking appropriate precautions to prevent evaporation of the sample prior to analysis. Preferably the concentration of methanol can be determined by a GC analysis of the feed with suitable calibration for oxygenates.

Products obtained from the distillation zone include a light gaseous product composed primarily of methane and ethane, a C3–C4 olefin-containing stream, a C5–300° F. product and a 300° F.+ product. Prior to forwarding the C3–C4 olefin stream to the alkylation zone, the olefin stream should be treated to lower the oxygenate level. It is an important feature of the invention that the amount of oxygenate in the C3–C4 olefin stream when it is admixed with the isobutane stream for alkylation, should be no more than 4000 ppm, preferably not more than 2500 ppm, and most preferably, 1000 ppm or below when expressed as a concentration of the olefin stream. If the C3–C4 olefin stream leaving the distillation zone has an oxygenate content above the 4000 ppm limit, the stream should be further processed to reduce the oxygenate content.

The oxygenates can be measured by GC-MS or simple GC. GC-MS is preferred. While the oxygen concentration is given in terms of oxygenates, it may also be given in terms of oxygen concentration. A limit of no more than 4000 ppm oxygenates, more preferably no more than 1000 ppm oxygenates, refer to the olefin stream to the alkylation plant. If the olefin stream is diluted with other streams, e.g. isobutane, the oxygenate determination is adjusted to account for the dilution, and is always expressed as a concentration of the olefin stream component alone.

In extractive distillation, an additional component is added to facilitate the separation. This mass-separating agent, or solvent, is fed into the distillation column near the top. Typically, the solvent has a low volatility and exerts a selective attraction for the oxygen-containing contaminants. This attraction results in an increased separation factor. The low solvent volatility insures that significant amounts of the solvent, typically 60 to 90 percent, are found on every stage or tray in the column. Solvent loaded with the oxygenate contaminant is removed at the bottom of the distillation tower and regenerated separately, by another distillation. An example of such a system is the separation of isobutane from butene using furfural as a solvent. For the removal of oxygenates from the Fischer-Tropsch liquids listed above, suitable solvents include high molelular weight carboxylic acids (e.g. neodecanoic acid and 2-ethyl-hexanoic acid) and alcohols such as octanol, 2-ethyl hexanol and decanol. Ionic liquids may be used for the removal of alcohols and acids. High molecular weight bases such as organic amines may be used to remove carboxylic acids. A further description of Extractive Distillation can be found in *Chemical Engineers' Handbook*, John. H. Perry, 4$^{th}$ Edition, Section 13 pages 46–55, incorporated herein by reference.

In azeotropic distillation an additional solvent is added. In this case the solvent selected forms a minimum boiling azeotrope with the contaminants. The azeotropic mix boils at a lower temperature than the other components and is carried overhead in the distillation column with the oxygen-free product going to bottoms. An industrial example of azeotropic distillation is the separation of ethanol from water using benzene. In an example, 11% water and 89% ethanol are fed to a distillation column and benzene added near the top of the column. Water-benzene-alcohol in a near azeotropic composition (22-54-24% respectively) are removed at the top of the column and pure ethanol is removed at the bottoms. The benzene is recovered by condensing the overhead vapor and allowing the immiscible benzene/water phase to split. Benzene (with some water and alcohol) is fed back to the column, and the water phase (containing some benzene and alcohol) further purified with additional distillation. For the removal of alcohols from Fischer-Tropsch liquids, suitable solvents include those solvents known to form azeotropic mixtures with the alcohol alone. For 1-propanol, these include dioxane, butyl formate, chlorobenzene, fluorobenzene, all isomers of xylene, toluene, methyl cyclohexane, and the like. A further description of Azeotropic Distillation can be found in Chemical Engineers' Handbook, John. H. Perry, 4$^{th}$ Edition, Section 13 pages 46–55, the disclosure of which is incorporated herein.

In addition to the propylene and butene in the $C_3$–$C_4$ fraction, a considerable amount of alcohols are present in the higher boiling range fractions. These alcohols are predominantly linear alcohols. They have good research octane values, but moderate motor octane values: n-propanol octane numbers are 117 research and 90 motor, n-butanol octane numbers are 95 research and 79 motor. Alcohols in this range normally retain water. When these alcohols are added to gasolines, the water will be absorbed into the gasoline and form a haze upon cooling. While in some situations the alcohols can be left in the naphtha product, it may be desirable to convert these alcohols into additional propylene and butenes by dehydration. These can then be added to the $C_3$–$C_4$ feed to the alkylation reactor. The $C_4$ olefins from a Fischer-Tropsch process will be predominately 1-butene with an isobutene content of less than 15 wt % preferably less than 10 wt % where these percentages are based on the total butenes.

The dehydration of alcohols to form olefins is a well-known chemical operation and representative methods have been described in the patent literature. U.S. Pat. Nos. 4,398,050, 4,547,601 and 4,260,841 disclose methods for dehydrating alcohols obtained in a Fischer-Tropsch synthesis. The disclosure of these patents are incorporated herein by reference. The preferred catalyst disclosed in the '050 patent for dehydration of alcohols is alkalized to prevent condensation and polymerization of the olefins. Catalysts preferred in this invention are not alkalized completely, and contain at least some acidity. Suitable catalysts may comprise any of the following: alumina, silica-alumina, zeolites, clays, etc.

Propanol and butanol present in other Fischer-Tropsch hydrocarbonaceous products can be separated from these hydrocarbonaceous fractions by extraction with water followed by distillation. This would produce a stream with a concentrated amount of propanol and butanol which could be dehydrated to form additional olefins.

Propanol and butanol will also be present in the aqueous phase that is a by-product of the Fischer-Tropsch reactor. These alcohols can be separated from the water by extraction with a light hydrocarbon, such as pentane, followed by distillation. Techniques for recovery of these alcohols from an aqueous stream are well-known and described in the article "Factors Influencing Solvent Selection for Extraction of Ethanol from Aqueous Streams," Curtis Munson and C. Judson King, I&EC Process Design and Development, 1984, Vol 23, pages 109–115. The propanol and/or butanol from any or all of these sources can be combined and fed to the dehydration zone to be converted to olefins.

Acetic and propanoic acids are possible oxygenate impurities in the light olefin feed to the alkylation zone. They may cause corrosion and catalyst fouling and it is desirable to remove these acids. Methods to remove organic acids from hydrocarbonaceous feeds are well known and include contacting with water, preferably water that has a pH>7.0, or by adsorption onto a solid, such as alumina, but preferably a solid that has some added alkali. Both the water washing and the adsorption on a solid are performed at near ambient conditions; for example, a temperature between 50° and 200° F., and a pressure between atmospheric and 500 psig. The amount of water or solid used in these processes relative to the hydrocarbonaceous feed depends on the relative contents of acids and alcohols. Sufficient water or solid should be used to remove the acid. Some experimentation may be required to determine the exact proportions for a given feed composition. The acids can also be destroyed in a separate process by conventional decarboxylation. Decarboxylation is a thermal reaction (not necessarily requiring a catalyst) and can occur simultaneously with dehydration. Suitable temperatures for decarboxylation are greater than 250° F., a pressure equal to or greater than atmospheric, and LHSV in the reactor of between 0.01 and 10 hr−1. The acids should be removed to the extent that they will no longer present a corrosion or catalyst problem.

The extent of acid removal can easily be evaluated by mixing one volume of hydrocarbon with 0.25 volumes of water that initially has a pH from between 6.5 and 7.5. The mixture is shaken at room temperature and the water phase collected and analyzed for pH. The extent of removal of acids is sufficient if the recovered water phase from this test is greater than 4.0, preferably greater than 5.0, and most preferably between 6.0 and 8.0. The pH value of the recovered water in this test is referred to as the acid value of the original hydrocarbon because direct measurement of acids in hydrocarbons is difficult and not as meaningful as a measure of the pH of the water that comes in contact with them.

As indicated previously, 2-butenes are more desirable than 1-butenes in the alkylation process. Accordingly, 1-butenes can be isomerized to 2-butenes using known procedures. U.S. Pat. Nos. 3,723,564 and 4,132,745 disclose isomerization methods to convert 1-butenes to 2-butenes. The disclosures of these patents are incorporated herein. $C_3$–$C_4$ light olefins containing alcohols can be simultaneously dehydrated and isomerized using a technique which is the subject of the invention in copending application Ser. No. 10/059,252, mentioned above.

Dehydration catalysts preferred for this invention can be identified by simple experiments using pure 1-butanol in small laboratory down-low units operated at atmospheric pressure and 1.0 LSHV with 0.2–0.4 grams of catalyst. The catalyst temperature is adjusted over the temperature range of about 300–600-F. to achieve 90% 1-butanol conversion, if possible. If measurements at precisely 90% are not generated, the results may be interpolated by a plot of the variables versus butanol conversion.

Examples of suitable catalysts are shown below.

|  | Broad | Preferred | Most Preferred |
|---|---|---|---|
| Temperature for 90% 1-Butanol Conversion, F. | 300–600 | 300–600 | 300–600 |
| 2-Butene content as % of total butenes | >10 | >50 | >75 |
| Selectivity of Butanol conversion to butenes | >50 | >50 | >90 |
| Catalyst | Solid oxides | Zeolites (ZSM-5,Y Zeolite) | 1-Dimensional 10-ring Zeolites (SSZ-32) |

A desired feature of these catalysts is the ability to suppress formation of $C_5+$ olefins. $C_5+$ olefins are formed if the catalyst is too acidic or has a structure that consists of 12-ring or intersecting 10-ring pores. $C_5+$ olefins have high octane and are not necessarily detrimental to the production of high octane gasoline blending streams; however, they have some undesirable features, and it is preferred to limit their formation. These undesirable features include increased air pollution during gasoline use, increased tendency to form oxidized products (gums) during gasoline storage, and reduced ability to form the desired high octane, highly branched isoparaffinic alkylate. Another desirable feature of these catalysts is that they suppress the saturation of olefins to form paraffins. The $C_4$ olefins can be saturated to form paraffins if hydrogen is present along with the feedstock. These paraffins will be normal paraffins and not suitable for alkylation. Catalysts which have high selectivities to the desired butene products (>90%) naturally have low selectivities to formation of other products such as $C_5+$ olefins and paraffins.

The most preferred class of catalyst are those that contain only 10-ring pores arranged in 1-dimension. Zeolites can be identified by determining their crystal structure by known methods. Zeolites are summarized in "Atlas of Zeolite Structure Types" prepared by the International Zeolite Association. Examples of structures (and common names) of zeolites and crystalline aluminophosphates of this type include: AEL (SM-3, SAPO-11), AFO (SAPO-41), EUO (EU-1), MTT (ZSM-23, SSZ-32), SFF (SSZ-44), STF (SSZ-35), TON (Theta-1, ZSM-22, SSZ-20). Other zeolites with structures not officially recognized but likely to be 1-D 10-ring pores include: ZSM-48, SUZ-4, IM-5, NU-88, SSZ-57, and ZSM-25. Of this list, MTT, TON and ZSM-48 are most highly preferred.

The following batch reactor technique was employed to identify suitable dehydration catalysts for conversion of 1-butanol into butenes, preferably 2-butene.

For each experiment, 1.0 g of catalyst was charged to a 25 mL stainless steel pressure batch reactor equipped with a magnetic stirring bar. The reactor was evacuated and back-filled with nitrogen several times. While under nitrogen, 5 mL of 1-butanol was added. The reactor was then heated with stirring for 18 hours at 200 C. Upon heating, the pressure rose to approximately 90–150 psig. At the end of the heating period, the reactor was cooled to room temperature and then to dry ice temperature. Through a rubber septum 5 mL of n-hexane was added. Next ~2 g of n-heptane was accurately weighed in to serve as an internal standard. The product was then removed from the reactor and analyzed by gas chromatography.

Samples of various acidic catalysts were evaluated in this batch test with the following results:

| Catalyst Identification | Zeolite Ring Aperture Size | Pore Dimensionality | Alpha Value | 1-Butanol conversion, % | Butene selectivity, % |
|---|---|---|---|---|---|
| CBV-760 Y zeolite | 12 | 3 | 28 | 77.9 | 5.6 |
| CBV-9010 Y zeolite | 12 | 3 | 3 | 83.3 | 9.5 |
| $Al_2O_3$-bound SSZ-32 | 10 | 1 | ~300 | 44.6 | 55.2 |
| $Al_2O_3$-bound ZSM-5 | 10 | 3 | 300 | 91.8 | 43.6 |

The preferred catalysts should have the highest possible values for 1-butanol conversion and selectivity for formation of butenes. The catalysts will have conversions and selectivities under conditions of this test equal to or greater than 25%, preferably equal to or greater than 40%, and most preferably equal to or greater than 75%. From this data, the preferred catalysts appear to be zeolites 10-ring apertures, and most preferably those with 1-dimensional pores.

The following flow micro reactor tests were employed to identify catalysts suitable for conversion of alcohols into olefins.

A flow-type microunit was equipped with a stainless steel fixed bed reactor and an on-line GC.

The catalysts studied here are as follows:

1. Alumina-bound Al-SSZ-32
2. Alumina-bound Al-ZSM-5
3. Alumina base (Condea Chemie, #20.301/90, as-provided by the supplier)
4. Alumina base (calcined in air at 950 F for 4 hours)

The catalysts (0.24–0.26 g=4.0 cc each) were crushed to 24–60 mesh and, prior to the reaction, dehydrated in a $N_2$ flow (200 cc/min) at 662 F (350 C) overnight.

The reactions were carried out in a down-flow mode at atmospheric pressure and 0.5/1.0 LHSV between 392 and 572 F. In one case (Al-SSZ-32), the reaction was carried out at 240 psig. No carrier gas such as $H_2$, $N_2$ or He was used during the reaction.

The products were analyzed with an on-line GC using a HP-1 capillary column and a FID. The FID Response Factors (RF) for 1-butanol, di-n-butyl ether and hydrocarbons were determined assuming hydrocarbon RF=1.

| Component | Response Factor (RF) |
|---|---|
| 1-butanol | 1.4663 |
| di-n-butyl ether | 1.2626 |
| octane (as internal standard) | 1.0000 |

The response factors are defined so that:

$$Wi = Woctane \times (Ai/Aoctane) \times (RFi/RFoctane)$$

where Wi stands for the weight of component i, Ai for the GC area of component i and RFi for the Response Factor of component i with RFoctane=1 for the internal standard octane.

Results from 1-butanol dehydration over alumina bound Al-SSZ-32:

| Temperature, F. | 482 | 482 | 482 | 392 | 410 | 410 |
|---|---|---|---|---|---|---|
| Pressure, psig | 0 | 0 | 0 | 0 | 0 | 240 |
| LHSV, h-1 | 0.5 | 1.0 | 2.0 | 1.0 | 1.0 | 1.0 |
| 1-Butanol Conversion, % | 100 | 100 | 100 | 7.7 | 24.8 | 17.9 |
| Yield, wt % | | | | | | |
| 1-Butene | 13.3 | 15.2 | 15.2 | 1.5 | 5.2 | 1.4 |
| cis-2-Butene | 24.0 | 30.7 | 31.5 | 1.8 | 6.2 | 3.3 |
| trans-2-Butene | 40.4 | 50.4 | 51.5 | 3.0 | 10.7 | 5.6 |
| iso-Butene | 0.9 | 0.5 | 0.5 | 0.1 | 0.1 | 0.1 |
| Total Butenes | 78.6 | 96.8 | 98.7 | 6.3 | 22.2 | 10.4 |
| Other products | 21.4 | 3.2 | 1.3 | 1.4 | 2.6 | 7.5 |
| Selectivity, wt % | | | | | | |
| 1-Butene | 13.3 | 15.2 | 15.2 | 19.1 | 21.0 | 7.8 |
| cis-2-Butene | 24.0 | 30.7 | 31.5 | 22.9 | 25.0 | 18.4 |
| trans-2-Butene | 40.4 | 50.4 | 51.5 | 38.5 | 43.2 | 31.3 |
| iso-Butene | 0.9 | 0.5 | 0.5 | 1.3 | 0.4 | 0.5 |
| Total Butenes | 78.6 | 96.8 | 98.7 | 81.8 | 89.6 | 58.0 |
| Other Products | 21.4 | 3.2 | 1.3 | 18.2 | 10.5 | 41.9 |

These results show that 1-dimensional 10-ring zeolite SSZ-32 gives conversions of 100% and selectivities to butenes of over 95%. Furthermore, the content of 2-butenes in the butene fraction is high and near equilibrium. Also, the content of iso-butene is low possibly due to the confined nature of the pores in this catalyst. Operation at pressures near atmospheric pressure is preferred since this gives the maximum selectivity to the desired butenes. In commercial practice, operation at exactly atmospheric pressure is not practical, but the pressure should be as low as possible, preferably below 100 psig, more preferably below 50 psig, and most preferably below 25 psig.

Results from 1-butanol dehydration over alumina bound Al-ZSM-5:

| Temperature, F. | 482 | 392 | 392 | 410 |
|---|---|---|---|---|
| Pressure, psig | 0 | 0 | 0 | 0 |
| LHSV, h-1 | 0.5 | 0.5 | 1.0 | 1.0 |
| 1-Butanol Conversion, % | 100 | 35.9 | 22.8 | 35.4 |
| Yield, wt % | | | | |
| 1-Butene | 11.9 | 4.7 | 4.0 | 4.8 |
| cis-2-Butene | 22.1 | 4.9 | 3.1 | 4.9 |
| trans-2-Butene | 36.3 | 7.4 | 4.8 | 7.2 |
| iso-Butene | 0.5 | 0.2 | 0.1 | 0.1 |
| Total Butenes | 70.8 | 17.2 | 12.0 | 17.0 |
| Other products | 29.2 | 18.7 | 10.8 | 18.4 |
| Selectivity, wt % | | | | |
| 1-Butene | 11.9 | 13.1 | 17.5 | 13.6 |
| cis-2-Butene | 22.1 | 13.7 | 13.6 | 13.8 |
| trans-2-Butene | 36.3 | 20.6 | 21.1 | 20.3 |
| iso-Butene | 0.5 | 0.6 | 0.4 | 0.3 |
| Total Butenes | 70.8 | 48.0 | 52.6 | 48.0 |
| Other Products | 29.2 | 52.1 | 47.4 | 52.0 |

In comparison to the 1-dimensional 10-ring zeolite SSZ-32, results using the 3-dimensional 10-ring zeolite ZSM-5 show poorer selectivities to the desired butene products. Thus, while it can be used, it is not a preferred catalyst.

Results from 1-butanol dehydration over the solid oxide alumina:

| Temperature, F. | 482 | 482 | 572 |
|---|---|---|---|
| Pressure, psig | ~0 | ~0 | ~0 |
| LHSV, h-1 | 1.0 | 0.5 | 0.5 |
| 1-Butanol Conversion, % | 15.9 | 18.6 | 85.1 |
| Yield, wt % | | | |
| 1-Butene | 1.4 | 2.2 | 67.3 |
| cis-2-Butene | 0.1 | 0.1 | 0.5 |
| trans-2-Butene | 0.1 | 0.1 | 1.7 |
| iso-Butene | 0 | 0 | 0.1 |
| Total Butenes | 1.6 | 2.4 | 69.6 |
| Other products | 14.3 | 16.3 | 15.5 |
| Selectivity, wt % | | | |
| 1-Butene | 8.8 | 11.7 | 79.1 |
| cis-2-Butene | 0.6 | 0.4 | 0.6 |
| trans-2-Butene | 0.6 | 0.4 | 2.0 |
| iso-Butene | 0 | 0 | 0.1 |
| Total Butenes | 10.0 | 12.5 | 81.8 |
| Other Products | 90.0 | 87.5 | 18.2 |

In comparison to the more acidic zeolites, alumina was less active and required higher temperatures to achieve conversions above 80%. In addition, the primary product from the dehydration of 1-butanol is 1-butene, which gives an inferior alkylate product in comparison to 2-butene. Thus, while alumina can be used as a dehydration catalyst, it is not the material of choice.

Results from 1-butanol dehydration over alumina (calcined):

| Temperature, F. | 482 | 482 | 572 |
|---|---|---|---|
| Pressure, psig | ~0 | ~0 | 0 |
| LHSV, h-1 | 1.0 | 0.5 | 0.5 |
| 1-Butanol | 41.7 | 54.0 | 100 |

-continued

| Conversion, %<br>Yield, wt % | | | |
|---|---|---|---|
| 1-Butene | 10.0 | 13.4 | 80.5 |
| cis-2-Butene | 0.1 | 0.2 | 5.6 |
| trans-2-Butene | 0.2 | 0.2 | 13.8 |
| iso-Butene | 0 | 0 | 0.1 |
| Total Butenes | 10.3 | 13.8 | 100.0 |
| Other products | 31.4 | 40.2 | 0 |
| Selectivity, wt % | | | |
| 1-Butene | 24.0 | 24.8 | 80.5 |
| cis-2-Butene | 0.2 | 0.4 | 5.6 |
| trans-2-Butene | 0.5 | 0.4 | 13.8 |
| iso-Butene | 0 | 0 | 0 |
| Total Butenes | 24.7 | 25.6 | 100.0 |
| Other Products | 75.3 | 74.4 | 0 |

Calcining the alumina prior to use increased its activity significantly. When operated at near 100% conversion of 1-butanol, selectivity to butenes was excellent. However, the predominant butene was again 1-butene and not the preferred 2-butenes. Thus, if alumina is used as the dehydration catalyst, it preferably should be calcined prior to use.

A preferred feature of the invention is to utilize a Fischer-Tropsch product to generate the isobutane stream used in the alkylation process. The stream should contain at least 30 wt. % isobutane, preferably at least 50 wt. %, and most preferably, at least 75 wt. %. As mentioned previously, the $C_4$ stream from a Fisher-Tropsch synthesis lacks sufficient levels of isobutane. The isobutane stream is generated by hydrotreating and hydrocracking the 300° F.+ product obtained from the distillation zone as previously described. The 300° F.+ product is transported from the distillation zone to a hydrotreatment/hydrocracking complex.

Hydrotreatment is a well-known technique designed to remove impurities such as elemental or compounds containing sulfur, nitrogen and oxygenates from carbonaceous products. Reaction conditions vary over a wide range and the selection of suitable conditions would be well within the purview of those skilled in the art. Typical hydrotreating conditions include temperature ranges of 300°–750° F., hydrogen to oil ratios of greater than 50 SCF/Bbl and overall LHSV of greater than 0.25 preferably about 1–4 $hr^{-1}$.

Effluent from the hydrotreating zone is forwarded to a distillation zone. Recovered fractions include light gases, a naphtha fraction, a distillate fuel fraction, a heavy hydrocarbon product and an isobutane-containing stream. The heavy hydrocarbons are circulated to a hydrocracker. Reaction conditions to achieve optimum hydrocracking would be within the purview of those skilled in the art. Hydrocracking is effected by contacting the fraction or combinations of fractions with hydrogen in the presence of a suitable catalyst at temperatures ranging from about 600°–900° F., pressures ranging from about 200–4000 psia and space velocities ranging from about 0.1–10 $hr^{-1}$. The hydrocracker effluent is then forwarded to a distillation zone from which various boiling range fractions are recovered, one of which is an isobutane fraction.

Alternatively, the isobutane feed can be obtained from other sources. A $C_4$ fraction obtained from natural gas or petroleum contains isobutane and n-butane. Since the isobutane/n-butane ratio typically is below 1, it is desirable to isomerize the $C_4$ paraffin fraction using conventional techniques to increase the level of isobutane.

The isobutane stream is forwarded to the alkylation zone. It may be admixed with the $C_3$–$C_4$ olefin stream before entering the alkylation zone or separate streams may be circulated to the zone. As indicated earlier, alkylation of olefins with isobutane is a well-known technology and extensively described in the literature as well as in many patents. Representative articles include the following: "Saga of a Discovery: Alkylation", Herman Pines, Chemtech, March 1982, pages 150–154; "The Mechanism of Alkylation of Paraffins", Louis Schmerling, Industrial and Engineering Chemistry, February 1946, pages 275–281; "The Alkylation of Iso-Paraffins by Olefins in the Presence of Hydrogen Fluoride", Carl B. Linn and Aristid V. Grosse, American Chemical Society, Cleveland Meeting, Apr. 2–7, 1944; "$H_2SO_4$, HF Processes Compared, and New Technologies Revealed", Lyle Albright, Oil and Gas Journal, Nov. 26, 1990. U.S. Patents which disclose methods of alkylating olefins with isoparaffins include the following: U.S. Pat. Nos. 6,194,625; 5,792,896; 5,654,251.

Key elements of the alkylation process include contacting a mixture of an isoparaffin (usually isobutane, but isopentane can also be used either by itself or as a mixture with isobutane) with an olefin (usually propylene and butenes but also pentene) in the presence of an acid catalyst. The most frequently used acid catalysts are sulfuric and hydrofluoric acids in liquid form. The pressure of the alkylation reaction using these acids should be sufficient to keep the olefins and isoparaffin in the liquid phase at reaction temperature. The reaction is exothermic, and inlet temperatures are near ambient conditions. Internal cooling is commonly used to remove the heat of reaction. Sulfuric acid alkylation plants typically operate at between 45° and 55° F. and use a refrigeration system to control the heat of reaction. Hydrofluoric acid plants typically operate at between 90° and 100° F. using cooling water to control the heat of reaction. The molar ratio of isoparaffin to olefin is greater than 1.0 in order to avoid polymerization. In general, typical molar ratios are above 4 and most typically between 4 and 12. When using sulfuric acid as the alkylation catalyst, typical ratios are between 5 and 10. With hydrofluoric acid, typical ratios are between 8 and 12. Contact times in the reactor are in excess of 1 minute but typically less than 1 hour, usually 10–40 minutes. After reaction, the hydrocarbon phase which consists of the alkylation product, unreacted isobutane and smaller amounts of unreacted olefin, is separated from the acid phase by density difference. The acid is recycled to the reactor, and may be cooled during this recycle operation. The hydrocarbon products are separated by distillation to recover the high boiling, high octane, highly branched isoparaffinic product and unreacted isobutane. The unreacted isobutane is recycled to the reactor. Both $H_2SO_4$ and HF catalysts will react with water in the feedstock and become diluted. With sulfuric acid, no special precautions need to be taken except for a coalescer to separate entrained water from the feed. With hydrofluoric acid, the feedstock is dried by passage over an adsorbent (typically a zeolite) to reduce the water content to low values (typically below 50 ppm, preferably below 10 ppm).

The invention will now be illustrated by the following example which is intended to be merely exemplary and in no manner limiting.

EXAMPLE

With reference to the FIGURE, a synthesis gas is reacted over a cobalt catalyst in a slurry bed Fischer-Tropsch reactor (10). The product from the reaction includes a gas phase and a waxy liquid phase. The gas phase is cooled in a separation zone (20) to condense hydrocarbons. Unreacted synthesis gas which is not condensed, is recycled to the Fischer-Tropsch reactor. Water contained in the gas phase is separated from the condensed hydrocarbons by density differences. The condensed hydrocarbons along with the waxy liquid are distilled in zone (30) to form a light gas product (containing methane and ethane), a $C_3$–$C_4$ stream that contains olefins and alcohols, a $C_5$-300° F. product that also contains propanol and butanol, and a 300° F.+ product. The $C_4$ olefins in the $C_3$–$C_4$ stream contain less than about 10 wt % isobutene. The $C_3$–$C_4$ stream is contacted with an equal volume of water in water wash apparatus (40) at 20° C. and separated. The oxygenate content of the $C_3$–$C_4$ stream is reduced to below 1000 ppm and the $C_4$ olefins contain less than about 10% iso-butene.

The 300° F.+ product is hydrotreated in reactor (50) over a sulfided NiMo/$Al_2O_3$ catalyst at 1500 psig, 700° F. and 1.0 LHSV to remove oxygenate and olefin impurities and the product distilled in apparatus (60) to form light gases (not shown), an isobutane-containing stream, naphtha, distillate fuel products and heavy hydrocarbons. The heavy hydrocarbons are hydrocracked in reactor (80) over a sulfided NiW/$SiO_2$—$Al_2O_3$ catalyst at 1.0 LHSV, 1500 psig, and a temperature sufficient to achieve 60% per-pass conversion below the 5% point of the heavy hydrocarbons as determined by ASTM procedure D-2887.

The isobutane-containing stream from the distillation unit (60) of the hydrotreater-hydrocracker complex is mixed with the $C_3$–$C_4$ olefin stream recovered from the water wash apparatus (40). The mixture is circulated to alkylation reactor (70) and alkylated using sulfuric acid, and the high octane alkylate stream recovered. The research octane number of the alkylate is 85 and higher, preferably 90 or higher, most preferably 93 and higher. Optionally, the mixture can be blended with naphthas recovered from the Fischer-Tropsch process and/or the hydrocracker (80) to produce a blend with a research octane number of 80 or higher, preferably 90 or higher. The products from alkylation, Fischer-Tropsch and hydrocracking steps do not contain significant quantities of aromatics (less than 1 wt %). The blends of these streams contain less than 10 wt % aromatics. Aromatics are undesirable in gasolines due to environmental concerns.

Research Octane Numbers are determined according to ASTM D2699: "Standard Test Method for Research Octane Number of Spark-Ignition Engine Fuels".

While the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A process for manufacturing a high octane alkylate comprising the steps of:
   (a) obtaining a $C_3$–$C_4$ light olefin fraction from a Fischer-Tropsch reactor;
   (b) treating the olefin fraction to reduce the oxygenate level to below about 4000 ppm;
   (c) mixing the olefin fraction with an isoparaffin stream obtained from a Fischer-Tropsch reaction containing at least 30 wt. % isobutane;
   (d) reacting the combined stream from step (c) in the presence of an alkylation catalyst; and
   (e) recovering a highly branched isoparaffinic alkylate having a research octane number of at least about 80.

2. A process according to claim 1, wherein the isoparaffin stream in step (c) is obtained by subjecting a 300° F.+ Fischer-Tropsch fraction to hydrotreating, hydrocracking, hydrodewaxing or combinations thereof.

3. A process according to claim 1, wherein the olefin fraction in step (b) has an oxygenate content of less than about 2500 ppm.

4. A process according to claim 3, wherein the oxygenate content of the olefin fraction is less than about 1000 ppm.

5. A process according to claim 1, wherein at least a portion of oxygenates present in the $C_3$–$C_4$ olefin fraction are removed by water washing, decarboxylation, adsorption, distillation or combinations thereof.

6. A process according to claim 5, wherein the distillation comprises extractive or azeotropic distillation.

7. A process according to claim 1, where the highly branched isoparaffinic alkylate has an octane number of at least about 90.

8. A process according to claim 7, wherein said alkylate has an octane number of at least about 95.

9. A process according to claim 1, wherein the olefin fraction used in step (c) has an acid value of at least 4.

10. A process according to claim 1, wherein lower alcohols are recovered from the Fischer-Tropsch reactor and dehydrated to form olefins which are added to said light olefin fraction.

11. A process according to claim 1, wherein the combined stream from step (c) comprises $C_3$ and $C_4$ olefins, having less than 1000 ppm oxygenates, and less than 10 wt % of isobutene as a percentage of the $C_4$ olefins.

12. A process of manufacturing an alkylate which is highly branched, has a high isoparaffin content and has an octane number of at least about 80, comprising:
   (a) reacting a mixture containing CO and $H_2$ in the presence of a Fischer-Tropsch catalyst;
   (b) recovering a mixture of hydrocarbonaceous products including a light olefin fraction containing propylene, 1-butene, and alcohols; a $C_5$ to 300° F. naphtha fraction containing alcohols; and a 300° F.+ fraction;
   (c) subjecting the 300° F.+ fraction to hydrotreating, hydrocracking, hydrodewaxing or combinations thereof and recovering a fraction containing at least about 30 wt. % isobutane;
   (d) removing at least a portion of the alcohols from the light olefin fraction;
   (e) optionally, treating the 1-butene in the light olefin fraction with an isomerization catalyst;
   (f) admixing the isobutane-containing fraction from step (c) with the light olefin fraction from step (d);
   (g) reacting the admixture from step (e) in the presence of a liquid phase alkylation catalyst; and
   (h) recovering said alkylate.

13. The process according to claim 12 wherein step (d) is performed by water washing, decarboxylation, distillation, absorption or combination thereof to reduce the oxygenate content to less than 4000 ppm.

14. A process according to claim 12, wherein the oxygenate content of the olefin fraction in step (e) is below 1000 ppm.

15. A process according to claim 12, wherein steps (d) and (e) are performed simultaneously.

* * * * *

UNITED STATES PATENT AND TRADEMARK OFFICE
CERTIFICATE OF CORRECTION

PATENT NO. : 6,743,962 B2
DATED : June 1, 2004
INVENTOR(S) : Dennis J. O'Rear et al.

It is certified that error appears in the above-identified patent and that said Letters Patent is hereby corrected as shown below:

Column 14,
Line 59, delete the word "absorption" and insert in place therefore the word
-- adsorption --.

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,743,962 B2
DATED : June 1, 2004
INVENTOR(S) : Dennis J. O'Rear et al.

It is certified that error appears in the above-identified patent and that said Letters Patent is hereby corrected as shown below:

Column 14,
Line 59, delete the word "absorption" and insert therefore -- adsorption --.

Signed and Sealed this

Seventh Day of December, 2004

JON W. DUDAS
*Director of the United States Patent and Trademark Office*